(12) United States Patent
Mault

(10) Patent No.: US 6,402,698 B1
(45) Date of Patent: Jun. 11, 2002

(54) METABOLIC CALORIMETER EMPLOYING RESPIRATORY GAS ANALYSIS

(76) Inventor: James R. Mault, 1580 Blakcomb Ct., Evergreen, CO (US) 80439

(*) Notice: Subject to any disclaimer, the term of this patent is extended or adjusted under 35 U.S.C. 154(b) by 0 days.

(21) Appl. No.: 09/601,589

(22) PCT Filed: Feb. 5, 1999

(86) PCT No.: PCT/US99/02448

§ 371 (c)(1),
(2), (4) Date: Sep. 19, 2000

(87) PCT Pub. No.: WO99/39637

PCT Pub. Date: Aug. 12, 1999

Related U.S. Application Data

(60) Provisional application No. 60/073,812, filed on Feb. 5, 1998, and provisional application No. 60/104,983, filed on Oct. 20, 1998.

(51) Int. Cl.[7] .................................................. A61B 5/08

(52) U.S. Cl. ........................ 600/532; 600/538; 600/531

(58) Field of Search ................................. 600/529, 531, 600/532, 533, 538; 73/233; 128/204.22, 204.23

(56) References Cited

U.S. PATENT DOCUMENTS

| | | |
|---|---|---|
| 2,630,798 A | 3/1953 | White et al. |
| 2,826,912 A | 3/1958 | Kritz |
| 2,831,348 A | 4/1958 | Kritz |
| 2,838,399 A | 6/1958 | Vogel, Jr. |
| 2,869,357 A | 11/1959 | Kritz |
| 2,911,825 A | 11/1959 | Kritz |
| 2,920,012 A | 1/1960 | Sanders et al. |

(List continued on next page.)

FOREIGN PATENT DOCUMENTS

| | | |
|---|---|---|
| DE | 198 10 476 | 9/1998 |
| EP | 0459647 A1 | 12/1991 |
| EP | 0 712 638 | 12/1995 |
| GB | 2323292 | 9/1998 |
| WO | WO 96/40340 | 12/1996 |

OTHER PUBLICATIONS

Medical Progress Through Technology, vol. 9, No. 1, 1982 Berlin (D); pp. 27–32, R. Salminen et al., "Computerized Breath–By–Breath Analysis of Respiratory Variables During Exercise".

British Journal Of Anaesthesia, vol. 49, 1977 London (GB) pp. 575–587, J. A. Bushman et al. "Closed Circuit Anaesthesia".

IEEE Transactions on Biomedical Engineering, vol. 35, No. 9, Sep. 1988, pp. 653–659, Capek et al., "Noninvasive Measurement of Cardia Output Using Partial CO2 ReBreathing".

Clinics in Chest Medicine (Review), vol. 10, 1989, pp. 255–264, Heigenhauser et al., "Meausurement if Cardiac Output by Carbon Dioxide Rebreathing Methods".

*Primary Examiner*—Eric F. Winakur
*Assistant Examiner*—Navin Natnithithadha
(74) *Attorney, Agent, or Firm*—Gifford, Krass, Groh, Sprinkle, Anderson & Citkowski, P.C.

(57) ABSTRACT

An indirect calorimeter for measuring the metabolic activity and related respiratory parameters of a subject includes a facial mask operative to be supported in contact with the subject so as to pass the inhalations and exhalations as the patient breathes. Both the inhaled and exhaled gasses pass through a tube which incorporates an ultrasonic pulse transit time flow meter adapted to generate electrical signals as a function of the instantaneous flow volume. A fluorescence quench oxygen sensor is supported in the flow tube and generates electrical signals as a function of the instantaneous oxygen content of the respiratory gasses. A computation unit receives output signals from the flow sensor and the oxygen sensor to calculate oxygen consumption and related parameters.

34 Claims, 2 Drawing Sheets

U.S. PATENT DOCUMENTS

| | | |
|---|---|---|
| 3,212,684 A | 10/1965 | Seaton et al. |
| 3,220,255 A | 11/1965 | Scranton et al. |
| 3,250,270 A | 5/1966 | Bloom |
| 3,523,529 A | 8/1970 | Kissen |
| 3,681,197 A | 8/1972 | Smith |
| 3,726,270 A | 4/1973 | Griffis et al. |
| 3,799,149 A | 3/1974 | Rummel et al. |
| 3,814,091 A | 6/1974 | Henkin |
| 3,834,375 A | 9/1974 | Sanctuary et al. |
| 3,895,630 A | 7/1975 | Bachman |
| 3,938,551 A | 2/1976 | Henkin |
| 3,962,917 A | 6/1976 | Terada |
| 3,979,480 A | 9/1976 | Williams |
| 4,051,847 A | 10/1977 | Henkin |
| 4,078,554 A | 3/1978 | Lemaitre et al. |
| 4,186,735 A | 2/1980 | Henneman et al. |
| 4,188,946 A | 2/1980 | Watson et al. |
| 4,197,857 A | 4/1980 | Osborn |
| 4,200,094 A | 4/1980 | Gedeon et al. |
| 4,211,239 A | 7/1980 | Raemer et al. |
| 4,221,224 A | 9/1980 | Clark |
| 4,230,108 A | 10/1980 | Young |
| 4,341,867 A | 7/1982 | Johansen |
| 4,359,057 A | 11/1982 | Manzella |
| 4,368,740 A | 1/1983 | Binder |
| 4,386,604 A | 6/1983 | Hershey |
| 4,425,805 A | 1/1984 | Ogura et al. |
| 4,440,177 A | 4/1984 | Anderson et al. |
| 4,444,201 A | 4/1984 | Itoh |
| 4,463,764 A | 8/1984 | Anderson et al. |
| 4,572,208 A | 2/1986 | Cutler et al. |
| 4,598,700 A | 7/1986 | Tamm |
| 4,608,995 A | 9/1986 | Linnarsson et al. |
| 4,619,269 A | 10/1986 | Cutler et al. |
| 4,648,396 A | 3/1987 | Raemer |
| 4,658,832 A | 4/1987 | Brugnoli |
| 4,753,245 A | 6/1988 | Gedeon |
| 4,756,670 A | 7/1988 | Arai |
| 4,781,184 A | 11/1988 | Fife |
| 4,796,639 A | 1/1989 | Snow et al. |
| 4,850,371 A | 7/1989 | Broadhurst et al. |
| 4,856,531 A | 8/1989 | Merilainen |
| 4,909,259 A | 3/1990 | Tehrani |
| 4,914,959 A | 4/1990 | Mylvaganam et al. |
| 4,917,108 A | 4/1990 | Mault |
| 4,955,946 A | 9/1990 | Mount et al. |
| 4,986,268 A | 1/1991 | Tehrani |
| 4,998,018 A | 3/1991 | Kurahashi et al. |
| 5,022,406 A | 6/1991 | Tomlinson |
| 5,038,773 A | 8/1991 | Norlien et al. |
| 5,038,792 A | 8/1991 | Mault |
| 5,040,541 A | 8/1991 | Poppendiek ................ 128/718 |
| 5,042,500 A | 8/1991 | Norlien et al. |
| 5,042,501 A | 8/1991 | Kenny et al. |
| 5,060,506 A | 10/1991 | Douglas |
| 5,060,655 A | 10/1991 | Rudolph |
| 5,060,656 A | 10/1991 | Howard |
| 5,069,220 A | 12/1991 | Casparie et al. |
| 5,072,737 A | 12/1991 | Goulding |
| 5,081,871 A | 1/1992 | Glaser |
| 5,095,900 A | 3/1992 | Fertig et al. |
| 5,095,913 A | 3/1992 | Yelderman et al. |
| 5,117,674 A | 6/1992 | Howard |
| 5,119,825 A | 6/1992 | Huhn |
| 5,178,155 A | 1/1993 | Mault |
| 5,179,958 A | 1/1993 | Mault |
| 5,214,966 A | 6/1993 | Delsing |
| 5,233,996 A | 8/1993 | Coleman et al. |
| 5,282,473 A | 2/1994 | Braig et al. |
| 5,285,794 A | 2/1994 | Lynch |
| 5,293,875 A | 3/1994 | Stone |
| 5,299,579 A | 4/1994 | Gedeon et al. |
| 5,303,712 A | 4/1994 | Van Duren |
| 5,309,921 A | 5/1994 | Kisner et al. |
| 5,326,973 A | 7/1994 | Eckerbom et al. |
| 5,355,879 A | 10/1994 | Brain |
| 5,357,972 A | 10/1994 | Norlien |
| 5,363,857 A | 11/1994 | Howard |
| 5,398,695 A | 3/1995 | Anderson et al. |
| 5,402,796 A | 4/1995 | Packer et al. |
| 5,419,326 A | 5/1995 | Harnoncourt |
| 5,425,374 A | 6/1995 | Ueda et al. |
| 5,450,193 A | 9/1995 | Carlsen et al. |
| 5,468,961 A | 11/1995 | Gradon et al. |
| 5,503,151 A | 4/1996 | Harnoncourt et al. |
| 5,570,697 A | 11/1996 | Walker et al. |
| 5,632,281 A | 5/1997 | Rayburn |
| 5,645,071 A | 7/1997 | Harnoncourt et al. |
| 5,647,370 A | 7/1997 | Harnoncourt |
| 5,676,132 A | 10/1997 | Tillotson et al. |
| 5,705,735 A | 1/1998 | Acorn |
| 5,754,288 A | 5/1998 | Yamamoto et al. |
| 5,789,660 A | 8/1998 | Kofoed et al. |
| 5,796,009 A | 8/1998 | Delsing |
| 5,800,360 A | 9/1998 | Kisner et al. |
| 5,816,246 A | 10/1998 | Mirza |
| 5,831,175 A | 11/1998 | Fletcher-Haynes |
| 5,834,626 A | 11/1998 | DeCastro et al. |
| 5,836,300 A | 11/1998 | Mault |
| 5,922,610 A | 7/1999 | Micheels et al. |
| 5,932,812 A | 8/1999 | Delsing |
| 6,010,459 A | 1/2000 | Silkoff et al. |
| 6,044,843 A | 4/2000 | O'Neil et al. |
| 6,162,180 A * | 12/2000 | Miesel et al. ................ 600/529 |
| 6,174,289 B1 * | 1/2001 | Binder ........................ 600/532 |
| 6,302,851 B1 * | 10/2001 | Gedeon ........................ 600/538 |

* cited by examiner

METABOLIC CALORIMETER EMPLOYING RESPIRATORY GAS ANALYSIS

This application claims benefit of provisional applications Nos. 60/073,812 filed Feb. 5, 1998 and 60/104,983 filed Oct. 20, 1998.

FIELD OF THE INVENTION

This invention relates to a respiratory instrument for measuring metabolism and related respiratory parameters by indirect calorimetry.

BACKGROUND OF THE INVENTION

U.S. Pat. Nos. 5,038,792; 5,178,155; 5,179,958; and 5,836,300 all to the same inventor as the present application disclose systems for measuring metabolism and related respiratory parameters through indirect calorimetry. These instruments employ bidirectional flow meters which pass both the inhalations and the exhalations of a user breathing through the instrument and integrate the resulting instantaneous flow signals to determine total full flow volumes. The concentration of carbon dioxide generated by the user is determined by either passing the exhaled volume through a carbon dioxide scrubber before it passed through the flow meter so that the differences between the inhaled and exhaled volumes is essentially a measurement of the carbon dioxide contributed by the lungs or by the measurement of the instantaneous carbon dioxide content of the exhaled volume with a capnometer and integrating that signal with the exhaled flow volume. The oxygen consumption can then be calculated.

The scrubber used with certain of these systems was relatively bulky and required replenishment after extended usage. The capnometers used with the instruments to measure carbon dioxide concentration had to be highly precise and accordingly expensive because any error in measurement of the carbon dioxide content of the exhalation produces a substantially higher error in the resulting determination of the oxygen contents of the exhalation.

SUMMARY OF THE INVENTION

The present invention overcomes these disadvantages of prior art indirect calorimeters by providing a respiratory calorimeter in which both the inhaled and exhaled flow volumes pass through a flow meter which provides an output representative of the instantaneous flow rate and the inhalations and exhalations also pass over an oxygen sensor in contact with the flow pathway which provides an output as a function of the instantaneous oxygen concentration in the flowing gas. These two signals are provided to a computer which integrates them to derive signals representative of the inhaled and exhaled oxygen volume. From these measurements the oxygen consumption, carbon dioxide production, respiratory quotient, caloric expenditure and related respiratory parameters are calculated and displayed.

The preferred embodiment of the invention utilizes an ultrasonic transit time flow meter and a fluorescence quench oxygen sensor. Both of these sensors operate upon the respiratory gasses as they pass through a flow tube with a substantially continuous, uninterrupted internal diameter so that the flow is substantially laminar. Previous indirect calorimeters, including those disclosed in the above-described U.S. patents, have employed flow measurement techniques that require protrusions in the flow path such as pressure differential transducers, hot wire transducers or the like. Great difficulties are encountered in maintaining a largely laminar flow in transducers of this type, resulting in inaccuracies in the flow measurement. The present invention preferably employs a volume flow meter which transmits ultrasonic pulses through the flow stream in a direction either parallel to the flow path or at least having a component parallel to the flow path. The transit time of the pulses is a function of the flow rate of the gas and because the interior diameter of the flow tube wall is substantially uninterrupted, laminar flow conditions are maintained providing a high uniformity of measurement.

The preferred embodiment of the invention directly measures the oxygen concentration in the inhaled and exhaled gasses passing through the flow tube by a technique which does not introduce any protuberances into the flow area and which may be positioned to measure the oxygen content in the same area in which flow is measured. Thus, unlike previous systems which require some linear separation between the point of flow measurement and the point of gas analysis, and accordingly would result in inaccuracies were the two to be integrated, the present system does not create any phase lag between the oxygen measurement and the flow measurement which would otherwise result in inaccuracies and the need for signal processing to correct for the displacement of the measurements. The preferred embodiment of the invention employs a fluorescence quench technique for oxygen measurement which utilizes a fluoresceable chemical disposed on the interior diameter of the flow wall in the area of ultrasonic pulse transmission. This fluorescent coating may be formed on the tube wall directly or supported on the end of a fiberoptic probe terminating in alignment with the interior diameter of the tube. This coating is subjected to exciting radiation from the exterior of the tube and the resulting fluorescence may be measured from the exterior. The fluorescence is quenched by oxygen passing over the coating and the percentage of oxygen in the flow tube can be instantaneously measured by the intensity of the fluorescence.

The flow tube is preferably formed as a disposable insert which may be inserted into a permanent, reusable structure which includes the ultrasonic transmitter and receiver and the fluorescence oxygen sensor. The fluorescent coating may be covered on the tube side with a microbial filter formed as part of the disposable insert. This filter prevents the fluorescent coating from being bacterially contaminated. The disposable insert is utilized to avoid the spread of disease from user to user in situations in which the indirect calorimeter is used by a succession of persons. The insert is preferably produced of an inexpensive material such as plastic.

In the preferred embodiment, the disposable insert is supported by a disposable breathing mask that covers the nose and the mouth of the user, allowing normal breathing over the measurement time. Most prior art devices have employed mouthpieces; however, it has been determined that in certain applications the mouthpiece can induce a mild form of hyperventilation which increases the user's energy consumption and results in erroneous metabolic readings. In one embodiment of the present invention, the metabolic measurement components are integrated with and are contained within the mask with no requirement for external connections. When the mask is attached to the user's head by straps, adhesive, or the like, it allows a full range of user movement during the measurement. Thus, it can be used during normal exercise to allow determination of the effect of that activity on respiratory parameters and may also be used to measure resting energy expenditure. The increased user comfort resulting from the elimination of connections between the mask and associated apparatus allows measurements to be made over longer periods of time and minimizes the labored breathing often associated with conventional respiratory masks which affects accurate measurement of energy expenditure.

The mask also preferably incorporates a nasal spreader on its interior surface which adhesively attaches to the nares of the user's nose and pulls them outwardly to enlarge the nose flow area and minimize the energy expenditure in breathing, which is often increased with conventional masks.

In an alternative form of the invention the computation unit and display and controls are supported in a separate desktop or hand held unit and connected to the sensors within the mask by highly flexible cables or wireless transmission such as infrared or RF.

BRIEF DESCRIPTION OF THE DRAWINGS

Other advantages and applications of the present invention will be made apparent by the following detailed description of preferred embodiments of the invention. The description makes reference to the accompany drawings in which.

DETAILED DESCRIPTION OF THE INVENTION

Figure 1:
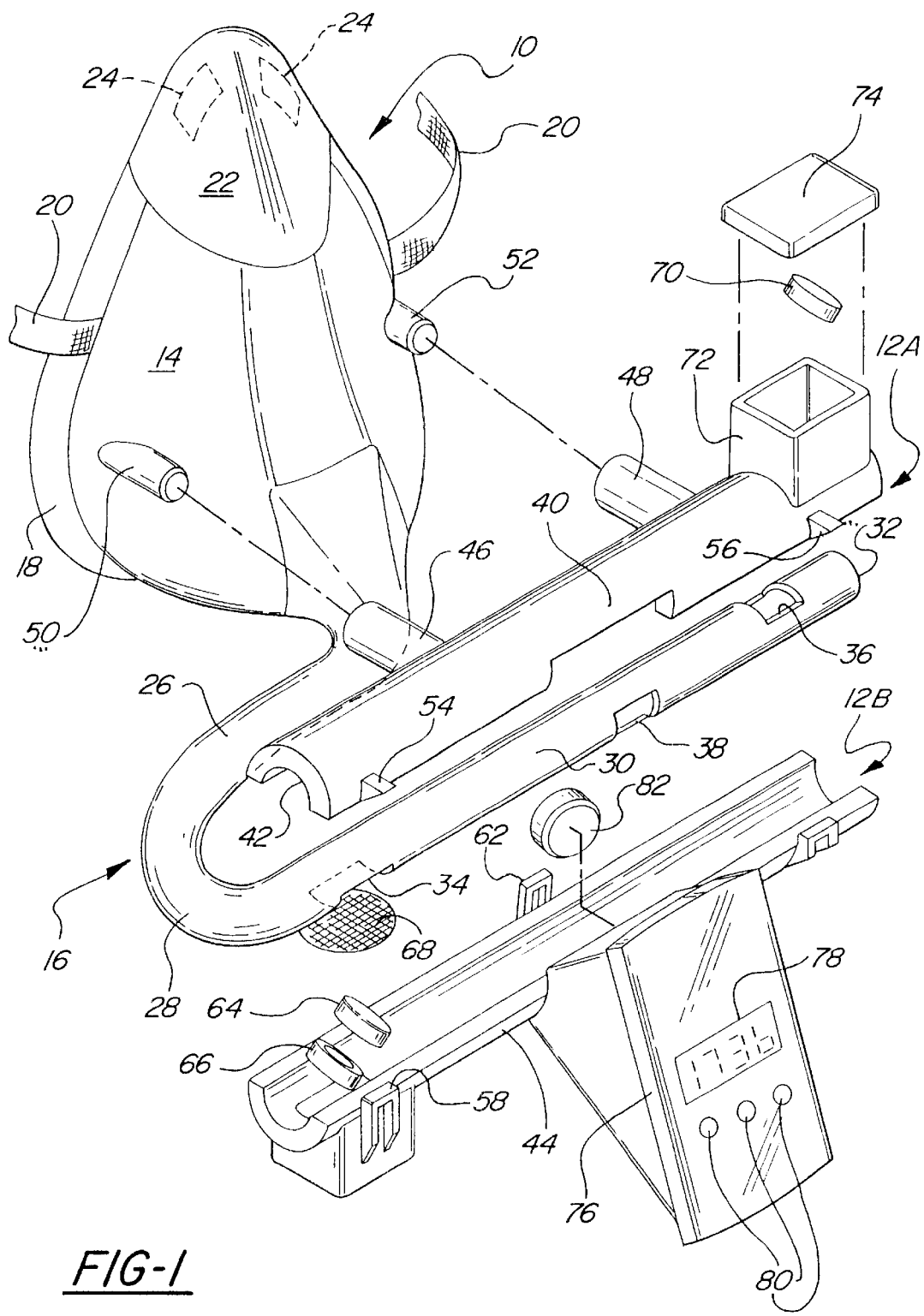
FIG. 1 is a perspective view in exploded form of a first embodiment of the invention.
Figure 2:
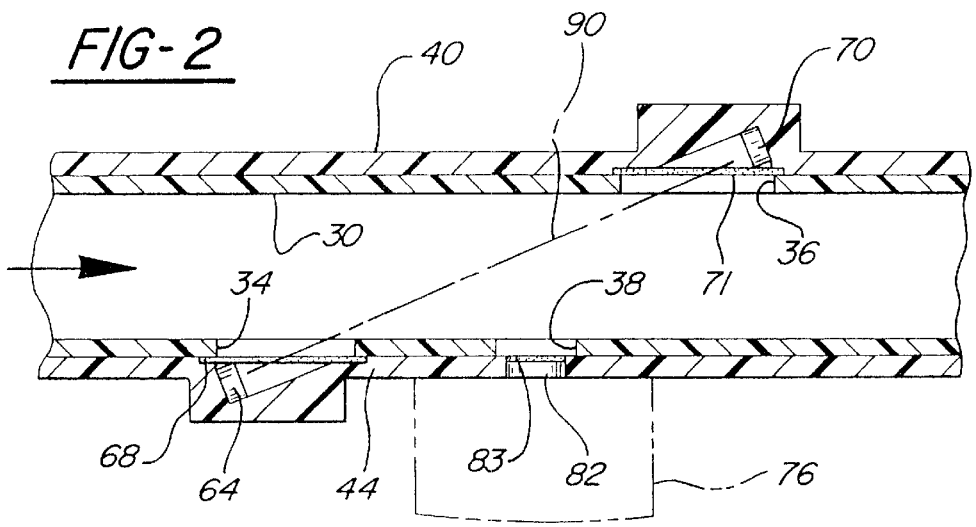
FIG. 2 is a cross-sectional view through the flow tube of FIG. 1.

Referring to FIGS. 1 and 2, a preferred embodiment of the invention includes a disposable section, generally indicated at 10, and a nondisposable section shown exploded into parts generally indicated at 12a and 12b. The disposable section 10 is made of low cost materials and is intended to be replaced when the calorimeter is employed by serial users to avoid hygiene problems such as transfer of bacterial infections. The disposable section 10 may be retained by a user for reuse at a later date or may be discarded. If the calorimeter is repeatedly used by a single user, the section 10 may not need to be discarded between uses. The section 10 broadly consists of a mask 14 and a U-shaped breathing tube generally indicated at 16. The mask is adapted to be retained over a user's face so as to cover the user's nose and mouth. The mask 14 has a resilient edge section 18 which engages the user's face in an airtight manner. The mask may be supported against the user's face by the user holding the outer side, but preferably the mask has straps 20 which connect to its edges and pass around the rear of the user's head. Alternatively, the mask could be retained by a pressure sensitive coating formed on the edge seal 18.

The mask proper is preferably formed of a rigid plastic but the section 22 at the top of the mask which is intended to surround the user's nose, is preferably formed of a more resilient material. Pressure sensitive adhesive pads 24 are formed on the interior surfaces of the nose section 22 and allow the user to press the outer surfaces of the nose section together so as to engage the outer surfaces of the user's nares with the pressure sensitive pads 24. When the pressure on the outer surface of the nose section 22 is released, the sections will spring outwardly and will pull the nares away from the nose so as to enable easy breathing through the nose into the mask.

The U-shaped breathing tube 16 connects to the interior of the mask 14. The tube then extends from the lower forward section of the mask and extends laterally as at 26 to the right of the user in a generally horizontal plane. At the extreme right it forms a 180 degree bight 28 and extends to the left of the user in an elongated measurement section 30. The far end of the tube 16 is opened at 32 so that as the user inhales while wearing the mask 14 air is drawn into the tube 16 through the end 32 and as the user exhales air is expelled through the end 32. The straight section 30 of the tube has three windows or openings, one, 34, formed at its lower side adjacent to the bight 28, the second, 36, formed on its upper side adjacent to the opening 32 and a third, 38, formed on the side of the tube in the middle of the section 30.

The nondisposable portion of the calorimeter consists of the interlocking upper section 12a and lower section 12b. The upper section 12a is formed about a semni-cylindrical section of tube 40. The inner diameter 42 of the tube section 40 matches the outer diameter of the disposable tube section 30 and the section 40 is slightly shorter than the straight line tube section 30. Similarly, the nondisposable section 12b is formed of a semi-cylindrical tube half 44 having an inner diameter matching the outer diameter of the tube section 30 and having a slightly shorter length.

The tube section 40 is formed with two rearward facing tubular supports 46 and 48, spaced along its length. These supports removably engage bosses 50 and 52 which are formed integrally with the face mask 14 and project forwardly from its upper sides. The lower tube section 44 is then locked to the upper tube section 40 so as to surround the breathing tube section 30. Cam sections 54 and 56 formed at the forward end of the tube section 40 engage latches 58 and 60 formed on the lower tube half and a similar cam (not shown) projecting from the rear of the tube 40 engages a latch 62 formed at the rear of the lower tube section 44 adjacent its free edge.

An ultrasonic transceiver 64 which is housed in a ring 66 formed in the lower tube section 44 projects into the window 34 of the tube section 30. An anti-microbial filter 68 covers the surface of the transducer 64. Similarly, an ultrasonic transducer 70 supported within a section 72 formed on the upper tube 40, and protected by a cover 74, projects into the window 36 adjacent the outlet and inlet end of the tube 30. An anti-microbial filter (not shown) may protect the surface of the transducer. The lower tubing section 44 is integrally formed with a housing 76 which contains the microprocessor which receives the signals from the transducers and sensors and controls their operation, and computes the oxygen consumption and other respiratory factors measured by the device. The unit 76 includes a display 78 and control switches 80. In certain embodiments of the invention a digital keypad may be included on the unit 76.

The computation unit determines oxygen consumption by solving the equation $VO_2=V_1\times(F_1O_2)-V_E\times(F_EO_2)$ where $VO_2$ is the consumed oxygen, $V_1$ is the inhaled volume, $V_E$ is the exhaled volume, $F_1O_2$ is the fraction of oxygen in the inhalation, and $F_EO_2$ is the fraction of volume in the exhalation. The system integrates the instantaneous flow volumes with the instantaneous oxygen levels over an entire breathing cycle, which is typically three to ten minutes. The system calculates carbon dioxide production in accordance with the following equation:

$$V_{CO_2}[V_E-(V_E \cdot F_E O_2)]-[V_1-(V_1 \cdot F_1 O_2)]$$

Other respiratory parameters such as RQ, REE, etc. may be calculated in the manner disclosed in my previous issued patents.

An oxygen concentration sensor 82 is supported within the housing 76 so that when the tube sections 40 and 44 are joined, the surface of the oxygen sensor, preferably covered with an anti-microbial filter 83, is disposed within the window 38 so that its outer surface is substantially flush with the internal diameter of the tube section 30. In alternate embodiments of the invention the fluorescent chemical, which is formed on the end of the oxygen concentration sensor 82 in the preferred embodiment, could be coated directly on the interior diameter of the tube section 30 and the fluorescence stimulating radiation and sensing of the resulting fluorescence intensity could be performed through a suitable window in the wall of the tube 30.

In use, a subject dons the mask 14 and attaches the straps so that the subject's nose is disposed within the section 22 of the mask, the subject's mouth is covered, and the area surrounding the mouth and nose are sealed by contact of the section 18 with the subject's face. The subject then pinches the outer surface of the section 22 of the mask so that the adhesive pads 24 are brought into pressured contact with the two sides of the subject's nose. The resilient section 22 is released so that the nares are separated, allowing free breathing within the mask.

Either prior to donning the mask or subsequently, the nondisposable sections 12a and 12b are attached so as to surround the tube 30 and the connecting sections 46 and 48 are attached to the bosses 50 and 52 on the front surface of the mask 14.

The user may then breathe in a normal manner so that the inhalations and exhalations are passed through the tube 16 and connect to the atmosphere at the tube end 32. After the subject has breathed through the mask for a minute or two to stabilize the breathing, one of the buttons 80 is depressed to start the measuring cycle. In alternative embodiments of the invention, rather than manually depressing the button 80 to start the measuring cycle, the computation unit 76 could sense the flow of gasses through the tube 30 and automatically initiate the measurement cycle when the breathing reached a normal level.

The ultrasonic transducers 64 and 70 face each other and transmit and receive ultrasonic pulses along a path 90 illustrated in FIG. 2 or some alternative path which is either parallel to or has a substantial component in the direction of the flow. The gas flow acts to advance or retard the flow of the pulses so that the full transmit time of the pulses is a function of the flow rate. The system preferably employs an ultrasonic flow meter manufactured by NDD Medizintechnik AG, of Zurich, Switzerland, and disclosed in U.S. Pat. Nos. 3,738,169; 4,425,805; 5,419,326; and 5,645,071.

The oxygen concentration center 82 is preferably of the fluorescent quench type as disclosed in U.S. Pat. Nos. 3,725,658; 5,517,313 and 5,632,958. The preferred embodiment may employ a sensor manufactured by Sensors for Medicine and Science, Inc. of Germantown, Maryland. The computation unit includes a source (not shown) for directing exciting radiation to the fluorescent coating on the end of the oxygen sensor 82 from exterior of the tube 30 and sensing the resulting fluorescence intensity which is diminished as a function of the concentration of oxygen and gas flowing over its surface to produce a direct measurement of oxygen concentration. The exciting radiation and fluorescent signal may be carried to the sensor by an optical fiber (not shown). In practice, after a user's breathing has stabilized and a test cycle is initiated either automatically or through manual depressions of one of the buttons 80, the flow rate and oxygen levels through the tube 30 are monitored by the sensors and provided to the computation unit. At the end of the cycle, which is preferably automatically timed, the measured quantity such as oxygen consumption will be shown on the display 78.

Figure 3:
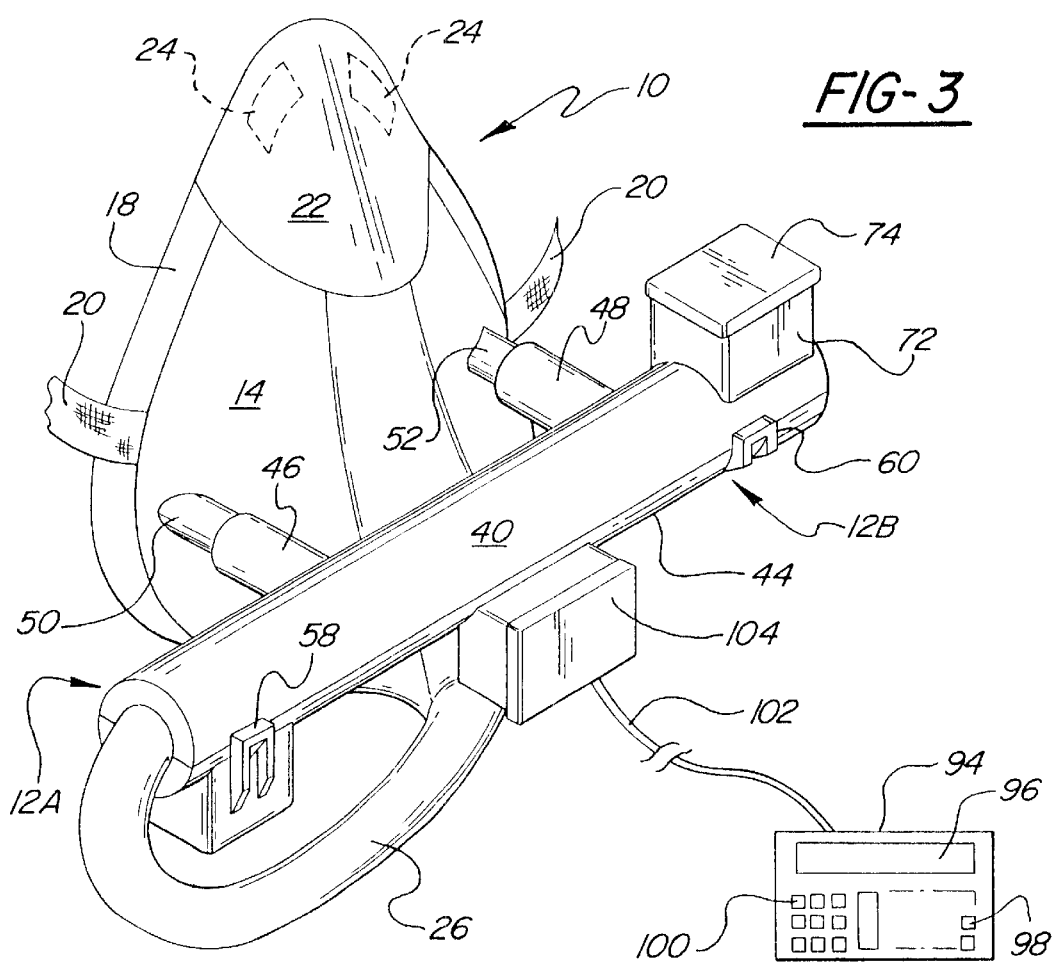
FIG. 3 is a perspective view of a second embodiment employing a desktop computation and display unit.

FIG. 3 illustrates an alternative embodiment of the invention in which the computation and display unit, 76, instead of being incorporated integrally with the nondisposable section which is secured to the master in use, is formed in a separate desktop unit 94. The unit incorporates a display 96, control switches 98, and a keyboard 100. It is connected to the section 12a by a flexible electrical cable 102. This arrangement lowers the weight of the unit which must be supported on the mask 14 during testing and allows more convenient user control of the unit and observation of the display. The computation and control unit 76 of the first embodiment is replaced in the embodiment by a box 104 which includes a connector for the cable 102 and also supports the oxygen sensor 82 in the same manner as the embodiment illustrated in FIG. 1. Otherwise, the system of FIG. 3 is identical to the system of FIG. 1 and similar numerals are used for similar sections.

What is claimed is:

1. An indirect calorimeter for measuring the metabolic activity of a subject, said analyzer comprising:
   a respiratory connector-operative to be supported in contact with the subject so as to pass inhaled and exhaled gases as the subject breathes;
   a flow tube connected at one end to the respiratory connector and at the other end to a source and sink for respiratory gases so as to receive and pass inhaled and exhaled gases;
   a flow meter operatively connected to said flow tube and adapted to generate electrical signals as a function of the instantaneous volume of inhaled and exhaled gases passing through the flow tube;
   an oxygen sensor supported on the flow tube so as to generate electrical signals as a function of the instantaneous fraction of oxygen in the inhaled and exhaled gases as they pass through the flow tube; and
   a computation unit for receiving said electrical output signals from the flow sensor and the oxygen sensor and operative to integrate the electrical signals which are functions of the instantaneous volume of gases passing through the flow tube with the electrical signals which are functions of the instantaneous fraction of oxygen in the gasses passing through the flow tube as the subject breathes over a period of time, the computation unit being operative to compute the oxygen consumption of the subject over the period of time by calculating the integral of the instantaneous flow volumes during inhalation, multiplied by the instantaneous oxygen content measurements at the time of such instantaneous flow volumes, and subtracting from that integral the integral of tile instantaneous flow volume during exhalation multiplied by the instantaneous oxygen content measurements at the time of such instantaneous flow volumes.

2. The indirect calorimeter of claim 1, wherein said flow meter is a bidirectional flow meter.

3. The indirect calorimeter of claim 2, wherein said bidirectional flow meter comprises an ultrasonic flow meter.

4. The indirect calorimeter of claim 1, wherein said oxygen sensor is a fluorescence quench oxygen sensor.

5. The indirect calorimeter of claim 1, wherein said respiratory connector comprises a mask having a free edge which can form a seal about a portion of a subject's face.

6. The indirect calorimeter of claim 5, wherein said bidirectional flow meter and said ultrasonic oxygen sensor are supported on said mask.

7. The indirect calorimeter of claim 6, wherein said bidirectional flow meter and said ultrasonic oxygen sensor are supported by an insert, said insert adapted to matingly engage at least a portion of said mask.

8. The indirect calorimeter of claim 5, wherein said mask comprises a digital processor, visual display, and a power source.

9. The indirect calorimeter as in claim 7, wherein said insert comprises at least two nares spreaders adapted to resiliently engage the nares to enlarge opening of the nares.

10. The indirect calorimeter of claim 9, wherein said nares spreader comprises outwardly biased adhesive regions which engage the user's nares and resiliently spring outwardly to enlarge the opening of the nares.

11. The indirect calorimeter of claim 5, wherein said mask further comprises a mechanism for transferring output from said sensors to said computer/computation unit.

12. The indirect calorimeter of claim 11, wherein said mechanism comprises a conductive line.

13. An indirect calorimeter comprising:
a permanent, reusable section;
a disposable section adapted to engage said permanent section;
an oxygen sensor disposed on said permanent section, said oxygen sensor including an emitter for stimulating radiation for a fluorescing coating, a receiver measuring the intensity of the fluorescing radiation emitted by said coating;
a flow meter disposed on said permanent section, said flow meter including an emitter of ultrasonic pulses and a detector for receiving reflected ultrasonic pulses; and
a computer/computation unit operative to receive outputs from said oxygen sensor and said flow meter and to calculate respiratory parameters.

14. The system of claim 1, wherein the computer further calculates the subject's carbon dioxide production over said period of time in accordance with the following equation:

$$V_{CO_2} = [V_E - (V_E \cdot F_E O_2)] - [V_1 - (V_1 \cdot F_1 O_2)]$$

15. The indirect calorimeter of claim 14, wherein said flow sensor is a bidirectional flow meter.

16. The indirect calorimeter of claim 14, wherein said gas sensor is an oxygen sensor.

17. The indirect calorimeter of claim 14, said flow meter including an emitter of ultrasonic pulses and a detector for receiving reflected ultrasonic pulses.

18. The indirect calorimeter of claim 16, wherein said oxygen sensor is a fluorescence quench oxygen sensor.

19. The indirect calorimeter of claim 18, wherein said oxygen sensor includes an emitter for stimulating radiation for a fluorescing coating and a receiver for measuring the intensity of the fluorescing radiation emitted by said coating.

20. The indirect calorimeter of claim 14, wherein said disposable section comprises a mask having a free edge which can form a seal about a portion of a subject's face.

21. The indirect calorimeter of claim 20, wherein said flow meter and said oxygen sensor are supported on said mask.

22. The indirect calorimeter of claim 21, wherein said flow meter and said ultrasonic sensor are supported by an insert, said insert adapted to matingly engage at least a portion of said mask.

23. The indirect calorimeter of claim 20, wherein said mask comprises a digital processor, visual display, and a power source.

24. The indirect calorimeter of claim 22, wherein said insert comprises at least two nares spreaders adapted to resiliently engage the nares to enlarge opening of the nares.

25. The indirect calorimeter of claim 24, wherein said nares spreaders comprise outwardly biased adhesive regions which engage the user's nares and resiliently spring outwardly to enlarge the opening of the nares.

26. The indirect calorimeter of claim 20, wherein said mask further comprises a mechanism for transferring output from said sensors to said computer/computation unit.

27. The indirect calorimeter of claim 26, wherein said mechanism comprises a conductive line.

28. The indirect calorimeter of claim 14, wherein said computer further calculates the subject's carbon dioxide production over said period of time in accordance with the following equation:

$$V_{CO_2} = [V_E - (V_E \cdot F_E O_2)] - [V_1 - (V_1 \cdot F_1 O_2)]$$

29. An indirect calorimeter for measuring the metabolic activity of a subject, said calorimeter comprising:
a respiratory connector configured to interface with the subject so as to pass inhaled and exhaled gases in use;
a flow pathway in fluid communication with the respiratory connector and with a source of respiratory gases and configured to pass inhaled and exhaled gases in use;
at least one flow meter provided along said flow pathway and adapted to generate electrical signals as a function of the instantaneous volume of inhaled and exhaled gases as said gases are actually passing through the flow pathway;
at least one oxygen sensor provided along said flow pathway and adapted to generate electrical signals as a function of the instantaneous fraction of oxygen in at least one of the inhaled and exhaled gases as said gases are actually passing through the flow pathway; and
a computation unit for receiving said electrical signals from the at least one flow meter and the at least one oxygen sensor and adapted to utilize said electrical signals to compute the subject's oxygen consumption over a period of time.

30. An indirect calorimeter for measuring the metabolic activity of a subject, said calorimeter comprising:
a respiratory connector configured to interface with the subject so as to pass inhaled and exhaled gases in use;
a flow pathway in fluid communication with the respiratory connector and with a source of respiratory gases and configured to pass inhaled and exhaled gases in use;
at least one flow meter adapted to determine the volume of inhaled and exhaled gases as said gases are passing through the flow pathway;
at least one oxygen sensor to determine the oxygen content of at least one of the inhaled and exhaled gases as said gases are passing through the flow pathway; and
a computation unit for receiving output signals from the at least one flow meter and the at least one oxygen sensor and adapted to utilize said output signals to compute the subject's oxygen consumption over a period of time.

31. An indirect calorimeter comprising:
a flow pathway adapted to communicate respiratory gases with a subject;
a permanent, reusable section having:
at least one flow meter adapted to measure the flow volume of gases as they pass through the flow pathway; and at least one gas sensor adapted to measure content of gases as they pass through the flow pathway;

a disposable section selectively engaged in fluid communication with said permanent section wherein said disposable section defines at least a portion of the flow pathway; and a respiratory connector configured to interface with a subject;

wherein said permanent section further comprises a computer/computation unit configured to receive outputs from said at least one gas sensor and said at least one flow meter and to calculate respiratory parameters therefrom.

32. An indirect calorimeter for measuring the metabolic activity of a subject, said calorimeter comprising:

a respiratory connector, wherein said respiratory connector is configured to interface with the subject;

a disposable section comprising:
  at least a portion of a flow pathway, wherein said flow pathway is in fluid communication with the respiratory connector and with a source of respiratory gases;

a permanent, reusable section adapted to selectively engage in fluid communication with said disposable section, said reusable section comprising:
  at least one flow meter, wherein said flow meter is adapted to measure flow volume of inhaled gases as they pass through the flow pathway and to measure flow volume of exhaled gases as they pass through the flow pathway;
  at least one oxygen sensor, wherein said at least one oxygen sensor is adapted to measure oxygen content in gases as they pass through the flow pathway; and a computer/computation unit operative to receive outputs from said at least one oxygen sensor and said at least one flow meter and adapted to compute the subject's oxygen consumption over a period of time.

33. A method for calculating oxygen consumption of a subject, comprising:

providing a flow tube through which the subject may inhale and exhale gas;

measuring within the flow tube the flow volume of inhaled gases as they pass through the flow tube;

measuring within the flow tube the flow volume of exhaled gases as they pass through the flow tube;

measuring within the flow tube the oxygen concentration of at least one of said inhaled and exhaled gases as they pass through the flow tube; and calculating oxygen consumption using the inhaled flow volume, the exhaled flow volume, and the oxygen concentration.

34. An indirect calorimeter operative to measure the respiratory consumption per unit time of a subject, comprising:

a respiratory connector operative to be in fluid communication with the respiratory system of a subject so as to pass respiratory gases as the subject breathes;

a flow meter operative to generate signals as a function of the volume of gases passed through the flow meter;

an oxygen sensor operative to generate signals as a function of the instantaneous oxygen content of gases passed through the sensor;

an electronic computer operative to receive signals from the flow meter and the oxygen sensor; and conduits interconnecting the respiratory connector, the flow meter and oxygen sensor such that the subject's inhalations and exhalations pass through the flow meter an the subject's exhalations pass through the oxygen sensor, the computer being operative to receive the signals from the oxygen sensor and the flow meter to calculate the subject's oxygen consumption over the period of the test.

* * * * *

UNITED STATES PATENT AND TRADEMARK OFFICE
CERTIFICATE OF CORRECTION

PATENT NO. : 6,402,698 B1
DATED : June 11, 2002
INVENTOR(S) : James R. Mault

It is certified that error appears in the above-identified patent and that said Letters Patent is hereby corrected as shown below:

Column 6,
Line 63, replace "5" with -- 1 --.
Line 64, delete "bidirectional".
Line 64, delete "ultrasonic".
Line 65, replace "supported on said mask" with -- disposed within said pathway --.
Line 66, replace "6" with -- 1 --.
Line 67, replace "bidirectional flow meter and said ultrasonic oxygen sensor supported by" with -- flow pathway includes --.

Column 7,
Line 3, replace "5" with -- 1 --.
Line 4, replace "mask" with -- computation unit --.
Line 6, replace "7" with -- 5 --.
Line 6, replace "wherein said insert comprises" with -- further comprising --.
Line 13, replace "5" with -- 1 --.
Lines 13-14, delete "wherein said mask"
Line 14, replace "comprises" with -- comprising --
Line 18, renumber claim "13" to -- 14 --.
Line 19, after "section" insert -- having sensors adapted to measure gases within a disposable section --.
Line 21, after "section" insert -- wherein said disposable respiratory gases between a subject's airway and a source of respiratory gases --.
Line 22, replace "an oxygen sensor disposed on said permanent section, said oxygen sensor including an emitter for stimulating radiation for a fluorescing coating, a receiver measuring the intensity of the fluorescing radiation emitted by said coating;" with -- a gas sensor disposed on said permanent section --.
Lines 27-28, after "section" delete -- said flow meter including an emitter of ultrasonic pulses --.
Line 31, replace "oxygen" with -- gas --.
Line 33, renumber claim "14" to -- 13 --.
Lines 33-37, move entire claim 13 (previously 14) before claim 14 (previously 13)
Line 33, replace "the" with -- said --.
Line 33, replace "computer" with -- computation unit --
Line 55, replace "20" with -- 14 --.
Line 56, replace "supported on said mask" with -- disposed within said flow path --.
Line 58, replace "21" with -- 14 --.
Line 59, replace "flow meter and ultrasonic sensor are supported by" with -- disposable section is --.
Line 62, replace "20" with -- 14 --.
Line 63, replace "mask" with -- computation unit --.
Line 65, replace "22" with -- 20 --.
Line 66, replace "insert" with -- mask --.

UNITED STATES PATENT AND TRADEMARK OFFICE
CERTIFICATE OF CORRECTION

PATENT NO.   : 6,402,698 B1
DATED        : June 11, 2002
INVENTOR(S)  : James R. Mault It is certified that error appears in the above-identified patent and that said Letters Patent is hereby corrected as shown below:

Column 8,
Line 5, replace "20" with -- 14 --.
Lines 5-6, replace "wherein said mask" with -- further --.
Line 6, replace "comprises" with -- comprising --.

Signed and Sealed this

Twenty-fifth Day of February, 2003

JAMES E. ROGAN
Director of the United States Patent and Trademark Office